US010737175B2

(12) United States Patent
Huang et al.

(10) Patent No.: US 10,737,175 B2
(45) Date of Patent: Aug. 11, 2020

(54) MOBILE AND ADAPTABLE FITNESS SYSTEM

(71) Applicant: Blue Goji LLC, Austin, TX (US)

(72) Inventors: Charles Huang, Los Altos, CA (US); Christopher A. Larkin, Los Gatos, CA (US); Steven S. L. Toh, Foster City, CA (US); Koley C. Porter, Austin, TX (US); Glenn F. Maynard, Austin, TX (US); Coleman F. Fung, Spicewood, TX (US)

(73) Assignee: BLUE GOJI LLC, Austin, TX (US)

( * ) Notice: Subject to any disclaimer, the term of this patent is extended or adjusted under 35 U.S.C. 154(b) by 1498 days.

(21) Appl. No.: 14/012,879

(22) Filed: Aug. 28, 2013

(65) Prior Publication Data

US 2014/0066201 A1    Mar. 6, 2014

Related U.S. Application Data

(60) Provisional application No. 61/696,068, filed on Aug. 31, 2012.

(51) Int. Cl.
*A63F 13/428* (2014.01)
*A63F 13/219* (2014.01)
(Continued)

(52) U.S. Cl.
CPC ........ *A63F 13/428* (2014.09); *A63B 24/0003* (2013.01); *A63F 13/04* (2013.01); *G06F 19/3481* (2013.01); *A63F 13/211* (2014.09); *A63F 2300/105* (2013.01); *A63F 2300/1012* (2013.01); *A63F 2300/1018* (2013.01); *A63F 2300/1043* (2013.01); *A63F 2300/6027* (2013.01); *A63F 2300/6045* (2013.01)

(58) Field of Classification Search
CPC ...... A63F 13/428; A63F 13/06; A63F 13/211; A63F 2300/1018; A63F 2300/1043; A63F 2300/6027; A63F 2300/6045; A63F 2300/1012; A63F 2300/105; A63B 24/0003; G06F 19/3481
See application file for complete search history.

(56) References Cited

U.S. PATENT DOCUMENTS

4,566,461 A    1/1986   Lubell et al.
4,735,410 A    4/1988   Nobuta
(Continued)

*Primary Examiner* — Sundhara M Ganesan
(74) *Attorney, Agent, or Firm* — Brian R. Galvin; Brian S. Boon; Galvin Patent Law LLC (57) ABSTRACT

A mobile and adaptable fitness system allows a fitness device to be used to control an application running on a host device. The system includes one or more controllers, a motion sensing device, and a host device. The hand controllers may be mounted on the handlebars of the fitness device or held in a user's hands and include buttons that the user can press. The motion sensing device may be mounted on the user or on a moving part of the fitness device and contains sensors that capture motion performed by the user. The host device receives input data from the hand controllers and the motion sensing device and generates an activity vector representing the intensity at which the user performs a fitness activity. Based on the activity vector, the host device controls an object in an application, such as a character, based on the input data.

2 Claims, 8 Drawing Sheets

(51) Int. Cl.
*A63B 24/00* (2006.01)
*G06F 19/00* (2018.01)
*A63F 13/211* (2014.01)

(56) References Cited

U.S. PATENT DOCUMENTS

| | | | |
|---|---|---|---|
| 4,790,528 A | 12/1988 | Nakao et al. | |
| 4,817,940 A | 4/1989 | Shaw et al. | |
| 4,867,442 A | 9/1989 | Matthews | |
| 4,911,427 A | 3/1990 | Matsumoto et al. | |
| 5,706,822 A | 1/1998 | Khavari | |
| 5,795,301 A | 8/1998 | Yasukawa et al. | |
| 5,879,270 A | 3/1999 | Huish et al. | |
| 5,976,083 A | 11/1999 | Richardson et al. | |
| 5,989,157 A | 11/1999 | Walton | |
| 6,002,982 A | 12/1999 | Fry | |
| 6,013,009 A | 1/2000 | Karkanen | |
| 6,126,571 A | 10/2000 | Parks | |
| 6,126,572 A | 10/2000 | Smith | |
| 6,244,988 B1 | 6/2001 | Delman | |
| 6,458,060 B1 | 10/2002 | Watterson et al. | |
| 6,471,622 B1 | 10/2002 | Hammer et al. | |
| 6,705,972 B1* | 3/2004 | Takano | A63B 24/00 482/7 |
| 6,830,540 B2 | 12/2004 | Watterson et al. | |
| 6,918,858 B2 | 7/2005 | Watterson et al. | |
| 6,997,852 B2 | 2/2006 | Watterson et al. | |
| 7,060,006 B1 | 6/2006 | Watterson et al. | |
| 7,060,008 B2 | 6/2006 | Watterson et al. | |
| 7,166,062 B1 | 1/2007 | Watterson et al. | |
| 7,166,064 B2 | 1/2007 | Watterson et al. | |
| 7,455,622 B2 | 11/2008 | Watterson et al. | |
| 7,556,590 B2 | 7/2009 | Watterson et al. | |
| 7,628,730 B1 | 12/2009 | Watterson et al. | |
| 7,645,212 B2 | 1/2010 | Ashby et al. | |
| 7,789,800 B1 | 9/2010 | Watterson et al. | |
| 7,981,000 B2 | 7/2011 | Watterson et al. | |
| 7,985,164 B2 | 7/2011 | Ashby | |
| 8,029,415 B2 | 10/2011 | Ashby et al. | |
| 8,251,874 B2 | 8/2012 | Ashby et al. | |
| 8,690,735 B2 | 4/2014 | Watterson et al. | |
| 2002/0016235 A1 | 2/2002 | Ashby et al. | |
| 2002/0165067 A1 | 11/2002 | Watterson et al. | |
| 2008/0051256 A1 | 2/2008 | Ashby et al. | |
| 2008/0214305 A1* | 9/2008 | Addington | A63B 22/16 463/36 |
| 2009/0163262 A1* | 6/2009 | Kang | A63B 24/0062 463/8 |
| 2010/0105525 A1* | 4/2010 | Thukral | A63B 24/0059 482/8 |
| 2011/0086707 A1* | 4/2011 | Loveland | A63B 24/0087 463/36 |
| 2011/0172059 A1 | 7/2011 | Watterson et al. | |
| 2013/0059698 A1 | 3/2013 | Barton | |
| 2013/0274067 A1 | 10/2013 | Watterson et al. | |
| 2013/0330694 A1 | 12/2013 | Watterson | |

* cited by examiner

MOBILE AND ADAPTABLE FITNESS SYSTEM

CROSS REFERENCE TO RELATED APPLICATIONS

This application claims the benefit of U.S. Provisional Application No. 61/696,068 filed Aug. 31, 2012, which is incorporated by reference in its entirety.

BACKGROUND

1. Field of Art

The disclosure generally relates to the field of electronic gaming, and in particular to using activity equipment as an electronic controller for a game.

2. Description of the Related Art

A user typically interacts with a fitness device, while either viewing or not viewing a static screen. For example, while running on a treadmill a user may choose to view a static screen displaying a television show. The elements in a television show are static, in that the elements do not change behavior based on the user's interactions with the television show, but instead perform predetermined actions. An example of a dynamic screen is that of a video game. The user interacts with a remote and influences the activity of the elements in the video game. At most the user may interact with the screen performing an activity independent of actions related to interacting with the fitness device. The disclosure of the invention addresses the problem of the user not being able to interact with elements on a screen while performing motions related to a fitness activity.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

An example mobile and adaptable fitness system allows a fitness device to be used to control an application running on a host device. The system includes one or more controllers, a motion sensing device, and a host device. The hand controllers may be mounted on the handlebars of the fitness device or held in a user's hands and include buttons that the user can press. The motion sensing device may be mounted on the user or on a moving part of the fitness device and contains sensors that capture motion performed by the user. The host device receives input data from the hand controllers and the motion sensing device and controls an object in an application, such as a character, based on the input data.

A mobile and adaptable fitness system provides a significantly enhanced fitness experience for users of standard gym and fitness equipment. This adaptable fitness system can be easily connected to and removed from standard and popular fitness devices such as a step machine, elliptical machine, treadmill and the like. The system turns a fitness device into a video game controller that can be used in an application connecting to an online service. Users of the adaptable fitness system can play games and track fitness performance on a mobile host device such as tablet or smartphone.

Overview of Adaptable Fitness System

Figure 1:
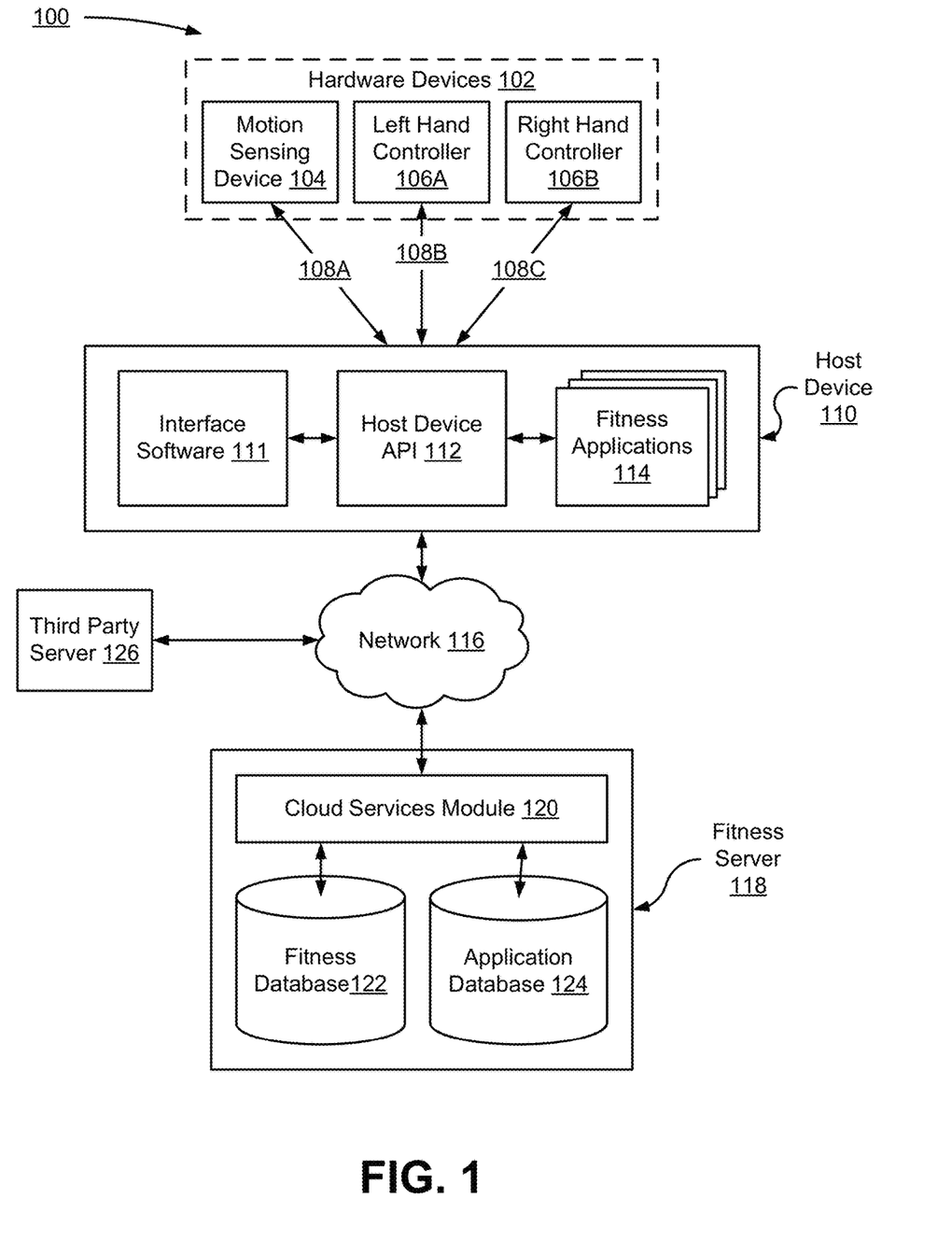
FIG. 1 is a block diagram illustrating components of the adaptable fitness system, according to one embodiment.

FIG. 1 is a block diagram illustrating components of the adaptable fitness system 100, according to one embodiment. The adaptable fitness system 100 includes a set of hardware devices 102, a host device 110, and a fitness server 118. In one embodiment, the hardware devices 102 generate a plurality of communication links 108A, 108B and 108C based on a user's interaction with the hardware devices 102. The host device 110 receives a plurality of data over the communication links 108A, 108B and 108C from the hardware devices 102 and interacts with a fitness application 114 or a plurality of fitness applications 114 based on the host devices' 110 interpretation of the data. The host device 110 communicates with the fitness server 118 over a network 116.

In one embodiment, the hardware devices 102 include a motion sensing device 104, a left hand controller 106A and a right hand controller 106B. The motion sensing device 104 captures a plurality of motion data in real-time, as the user interacts with the fitness system 100. The left hand controller 106A receives input from the user by way of an action, such as the user pressing a button on the controller or moving a joystick on the controller. The right hand controller 106B receives input from the user by way of an action, such as the user pressing a button on the controller or moving a joystick on the controller.

In alternative embodiments, additional hardware devices 102 may be used. For example, the hardware devices 102 may also include athletic shoes with embedded sensors or motion sensors that attach directly to the fitness system. In addition, some of the hardware devices shown 102 shown in FIG. 1 may be omitted. For example, only one of the hand controllers may be used, or the two hand controllers 106A, 106B may be replaced with a combined hand controller that contains the all of the buttons that would normally be distributed between the two hand controllers 106A, 106B.

In some embodiments, multiple sets of hardware devices 102 may be added to the system 100 to adapt additional fitness devices into additional game controllers. For example, multiple stationary bicycles may be adapted into controllers for a bicycle racing application, thus allowing multiple users to participate in virtual races against each other.

As a whole, the hardware devices 102 can be used to adapt a fitness device (e.g., a step machine, an elliptical machine, a treadmill, a rowing machine, etc.) into a game controller that receives a user's physical input (both motions and button presses) and generates corresponding input data for interacting with a fitness application 114. For example, the input data could be used to control a virtual character or object in the fitness application 114.

Input data from the hardware devices 102 are sent over communication links 108A, 108B, 108C (hereinafter referred to collectively as 108) to the host device API 112 on the host device 110. The communication links 108 may be wired or wireless connections. In one embodiment, the communications links 108 are based on the Bluetooth Low Energy (BLE) protocol, and the hardware devices 102 are BLE devices. If additional sets of hardware devices 102 are included in the system, additional communication links 108 are established to connect the hardware devices 102 to the host device 110.

In the illustrated embodiment, the communication links 108 connect each hardware device 102 directly to the host device 110. In this embodiment, the three hardware devices 102 connect simultaneously to the host device 110 over the communication links 108A, 108B, 108C. The hardware devices 102 may all connect over the same communication protocol (e.g., Bluetooth Low Energy), or over different communication protocols.

In another embodiment, only the motion sensing device 104 is connected directly to the host device 110 via the first communication link 108A. In this embodiment, the two hand controllers 106A, 106B are coupled to the motion sensing device 104 via the other two communication links 108B, 108C, and the motion sensing device 104 is configured to relay input data from the hand controllers 106A, 106B to the host device 110. This embodiment is described in more detail with reference to FIG. 2A.

The host device 110 includes interface software 111, a host device API 112, and one or more fitness applications 114. As a whole, the host device 110 is a computing device that is capable of executing program instructions. The host device 110 may be, for example, a smartphone, tablet computer, laptop computer, or desktop computer.

The interface software 111 and the host device API 112 operates in conjunction with the interface software to act as an interface between the hardware devices 102, the fitness applications 114, and the fitness server 118. When no hardware devices 102 are connected, the host device API 112 initiates a scan for hardware devices 102 at fixed intervals. Button presses on the hand controllers 106A, 106B or motion on the motion sensing device 104 will trigger the respective device to broadcast for connection (if not already connected). If the device's broadcast overlaps with one of the host device API's scanning intervals, then the host device API 112 initiates a connection attempt to the respective device. This process of establishing a connection after detecting a button press or motion allows for intuitive connection of hardware devices 102 to the host device 110. The host device API 112 maintains the connection between a fitness application 114 and a hardware device 102 as long as the application 114 remains active. After establishing a connection with one or more hardware devices 102, the interface software 111 and host device API 112 receive and process input data from the hardware devices 102 so that the input data can be used to control an application 114 or an object in an application 114. For example, the input data can be used by the application 114 to control a virtual character or object in a game.

The host device API 112 can distinguish the input data from the different hardware devices because the firmware of each hardware device can be configured to include an identifier (e.g., a binary value) in a header of any input data that is sent to the host device 110. Thus, the motion sensing device 106 would have a different identifier than the hand controllers 106A, 106B. The interface software 111 can then build a software state representation of each device based on the device's identifier, and the host device API 112 can map input data to its respective software state representation to identify the originating hardware device. After the input data is mapped, e.g., via a table or index, to the corresponding hardware device, the data can be used to as inputs to fitness applications 114. In embodiments where the motion sensing device 104 is configured to relay input data from the hand controllers 106A, 106B to the host device 110, the motion sensing device 104 may be configured to read the identifier in the input streams from the two hand controllers 106A, 106B and relay a single integrated input stream to the host device 110. This process is described in more detail with reference to FIGS. 2A and 2D.

In some embodiments, the left and right hand controllers 106A, 106B are manufactured to be identical (e.g., to reduce manufacturing costs) and have the same identifier. In these embodiments, it may be difficult to automatically distinguish between the input data from the two hand controllers 106A, 106B, so the interface software 111 may prompt the user to manually identify the two hand controllers (e.g., by first pressing a button on the left hand controller 106A and then pressing a button on the right hand controller 106B.) This setting can then be stored by the interface software 111 as part of the device's software state representation.

The interface software 111 can use a similar process to distinguish input data from different hardware devices when multiple sets of hardware devices are connected to the host device 110 (e.g., for a multiplayer game). For example, the interface software 111 may display a prompt to move a first motion sensing device 104 (e.g., attached to a stationary bicycle), then display a prompt to move a second motion sensing device 104 (e.g., attached to an elliptical trainer), and then display similar prompts to identify the respective hand controllers 106 on the two fitness devices.

In one embodiment, signals from the hand controllers 106A, 106B and motion sensing device 104 are wirelessly sent to the host device 110 as input data using a custom Bluetooth GATT profile. The data sent from the hardware devices 102 are then processed by the host device API 112.

An example of the dataflow between the hardware devices 102 and the host device 110 is presented below:

1. The motion sensing device 104 acts as a server and the host device 110 connects as a client.

2. The host device 110 (the client) subscribes to data notifications of a specific service feature of the motion sensing device 104, such as an accelerometer.

3. A reading from the service feature (e.g., an accelerometer reading) is taken from motion sensing device 104.

4. The reading is sent to the host device 110 (the client subscriber). For example, the three-axis accelerometer reading may be sent as three bytes.

5. The interface software 111 decodes the reading and makes the readings available to applications 114 via the API 112. The readings are interpreted as input data by the application 114 and allow users to make selections or to control/manipulate elements (e.g., objects, characters, etc.) within the application 114 or to react to game cues or other interactive elements within the application 114.

The fitness applications 114 are applications that receive input data from the hardware devices 102 through the host device API 112 and carry out some sort of user interaction based on the input data. For example, the fitness applications 114 can be exercise games or any non-game application that can interact with a fitness device in a meaningful way (e.g., an application 114 interact with hardware devices 102 mounted on a treadmill to simulate a walk through a park).

The applications 114 contain one or more objects. In one embodiment, the object is a graphical representation such as a car, a ball or a character. The object also exhibits a controlled behavior, such as the graphical representation of the ball may exhibit a behavior of rolling. As the user performs the fitness activity the graphical representation or the object exhibits a controlled behavior based on the fitness activity performed by the user. For example in one application the object can be a character representing the user. The character may exhibit a controlled behavior of running across the screen. The controlled behavior of running across the screen may be related to the speed at which the user runs. The faster the user runs the faster the character runs across the screen. Hence, the system allows the user to change and control the behavior of the object based on, in one instance, the intensity at which a user performs the fitness activity.

In another example the object is a set of numbers on a scoreboard. The number may represent a number of metrics, such as distance run by the user or the number of calories burned by the user. The numbers on the scoreboard exhibit a controlled behavior of changing at a rate related to the speed at which the user is running at. Hence the faster the user runs the rate at which the numbers on the scoreboard change increases.

In one embodiment, the input data received by the application 114 from the hardware devices 102 affects the behavior applied to the object in an application. Returning to the example of a character representing the user running across the screen; the user may press the button on the hand controller 106 causing the jumping behavior to be applied to the user's character in the application 114. This results in the user's character jumping over an obstacle as the user is playing the game. Hence, the user may also use the hardware devices 102 to apply a behavior to an object of the application 114.

Applications 114 (including games) may be configured to encourage the user to exercise. As the user exercises, data received from the hardware devices 102 is recorded on the host device 110 to reflect progress in the user's experience. Applications 114 can also connect to a fitness server 118 through the network 116, where user data and statistics can be stored and accessed.

One example of how the hardware devices 102 can interact with the software on the host device 110 could be a user attaching the motion sensing device 104 to the pedal of a stationary bicycle. An accelerometer in the motion sensing device 104 measures the motion of the pedals, allowing for realistic control of a 'virtual biking' application 114. Another example of how hardware devices 102 interact with software could be a user attaching the motion sensing device 104 to their hip, with the motion sensing device 104 detecting that motion for a dance or exercise game.

The host device API 112 may be configured to run on any suitable operating system, such as iOS, Windows/Mac/Linux or Android. Different versions of the host device API 112 may be created for different operating systems. Although shown as a separate entity within the host device 110, the host device API 112 is typically a separate code library that is compiled into a fitness application 114 at build time. This allows a third-party developer can write a fitness application 114 that uses functions in the host device API 112 to exchange data with the hardware devices 102 and the fitness server 118.

In one embodiment, the fitness server 118 is comprised of a cloud services module 120, a fitness database 122 and an application database 124. The fitness server 118 and its components 120, 122, 124 may be embodied as a single device or as a cluster of networked devices (e.g., a cluster of web servers). In one embodiment, the cloud services module 120 provides an interface over the network 116, by which the host device 110 can access fitness data from the fitness database 122 and application data from the application database on the fitness server 118. The cloud services module 120 receives historical data, such as physical activity and game performance data, from the host device API 112 and stores the data in the appropriate database 122, 124. For example, on installation of the fitness application 114 on a host device 110 running an Android operating system, the fitness application 114 may have to retrieve Android specific configuration and system commands from the application database 124 on the fitness server 118. In another example, the interface software 111 stores fitness data with respect to a specific user in the fitness database 122 on the fitness server 118. The user can now access the fitness data 122 on multiple host devices 110.

In one embodiment, the cloud services module 120 also allows users to access their information on any device and at any time. The module also processes user requests to compare and share scores on third-party servers 126, such as social networking systems, e.g., FACEBOOK and TWITTER. The databases 122, 124 may be stored across a cluster of several servers for scalability and fault-tolerance.

The cloud services module 120 can also host multiplayer games. In one embodiment, games are hosted in asynchronous context. After a user set ups a challenge, the cloud services module 120 can give a user a window in time to finish his "turn" or just wait until he completes a given goal. This information is stored in the application database 124. The cloud services module 120 executes the logic of the games, challenges, or goals that are created between players and maintains their states and progression.

In an alternative embodiment, the cloud services module 120 also hosts multiplayer games in real-time, with real-time game data moving back and forth between players on different host devices 110.

In another embodiment, a third party server 126 may communicate with the host device 110 or the fitness server 118 over the network 116. For example, the cloud services module 120 retrieves a user's social graph from a social networking system on a third-party server 126 and reproduces the social graph on the fitness server 118. Thus, subsequent functions associated with social game mechanics (e.g., the creation of challenges and cooperative goals) can be executed on the fitness server 118.

Motion Sensing Device Example

Figure 2A:
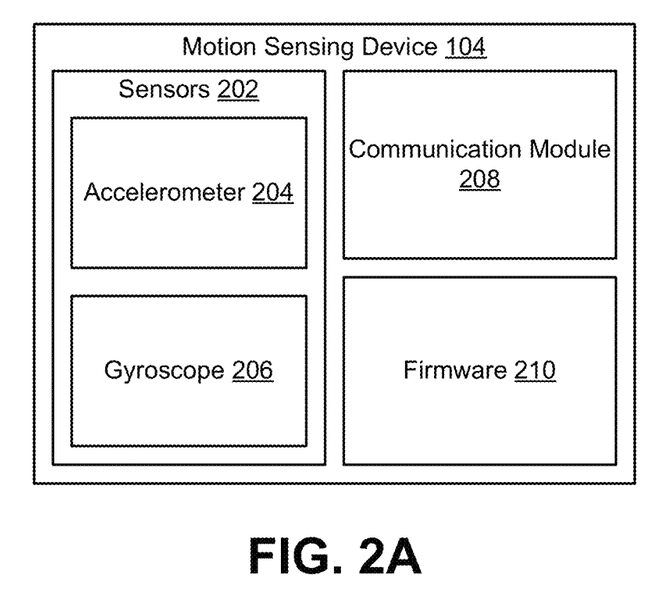
FIG. 2A is a block diagram illustrating the components of the motion sensing device, according to one embodiment.

FIG. 2A is a block diagram illustrating the components of the motion sensing device 104, according to one example embodiment. In this embodiment, the motion sensing device 104 includes sensors 202, a communication module 208, and firmware 210. However additional or different sensors 202 may be included in the motion sensing device 104. In one embodiment the user places the motion sensing device 104 on their body, such as on their arm, wrist, leg or ankle. In another embodiment, the user places the motion sensing device on the fitness system, such as on the handle bars of an elliptical machine.

The sensors 202 generate motion data based on an activity performed by the user. The activity performed by the user may include, running, cycling, using the elliptical machine, or any other form of exercise. In one embodiment the sensors 202 may include an accelerometer 204 and a gyroscope 206. In one embodiment, the accelerometer 204 captures acceleration data 204 based on the acceleration of the motion sensing device 104 along multiple axes. In one embodiment, the gyroscope 206 captures a rate of rotation of the motion sensing device 104 along multiple axes.

In one embodiment, the firmware 210 in the motion sensing device 104 is a combination of a persistent memory, a program stored in the memory and a set of hardware required to execute the program. The firmware 210 retrieves, formats and temporarily stores the data output by the accelerometer 204 and the gyroscope 206. In other embodiments the firmware 210 may perform other activities, such as controlling the rate at which data is retrieved from the accelerometer 204 and the gyroscope 206 or averaging samples of data retrieved from the accelerometer 204 and the gyroscope 206.

In another embodiment, the firmware 210 contains logic that manages the operation of the motion sensing device 104. For example, the firmware 210 may contain logic to support a "shake to connect" function that monitors the sensors 202 and establishes the communication link 108A to the host device 110 upon detecting that a user has shaken the motion sensing device 104.

In an alternative embodiment described with reference to FIG. 1, the two hand controllers 106A, 106B are coupled to the motion sensing device 104 and the motion sensing device 104 is configured to relay input data from the hand controllers 106A, 106B to the host device 110. In this alternative embodiment, the firmware 210 is configured to detect and connect to the hand controllers 106A, 106B independently of the host device 110, and the communication module 208 maintains the connections with the hand controllers 106A, 106B after they are established. The connections with the hand controllers 106A, 106B may be under the same communication protocol as the communication link 108A (e.g., Bluetooth Low Energy) or a different communication protocol (e.g., an RF connection). Meanwhile, the firmware 210 manages the three connections (the connections with the two hand controllers 106A, 106B and the communication link 108A with the host device 110) and relays input data from the hand controllers 106A, 106B to the host device 110. In some embodiments, the firmware 210 may be configured to combine the input data from the sensors 202 and the hand controllers 106A, 106B into a single integrated input stream. Thus, the host device API 112 receives a single input stream that includes inputs from all three hardware devices.

In one embodiment, the communication module 208 transmits the formatted acceleration and rate of rotation data from the firmware 210 to the host device 110. The communication module 208 interacts with the communication link 108A to transfer data between the motion sensing device 104 and the host device 110. In one embodiment, the communication module 208 connects via the Bluetooth Low Energy (BLE) protocol.

Figure 2B:
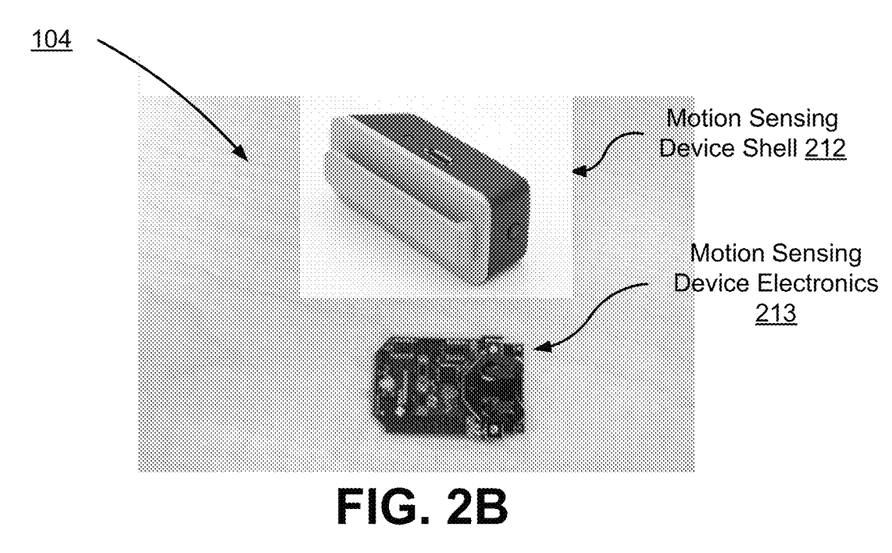
FIG. 2B illustrates a motion sensing device, according to one embodiment.

FIG. 2B illustrates a motion sensing device 104, according to another example embodiment. In this embodiment, the motion sensing device 104 is comprised of an electronic circuit 213, and an outer shell 212. The outer shell 212 houses the electronic circuit 213. The outer shell also contains an attachment mechanism to attach the motion sensing device 104 to the user or the fitness system. For example, the user can attach the motion sensing device 104 to their wrist, ankle or to the handle bars on an elliptical machine via the attachment mechanism. The electronic circuit is comprised of the accelerometer 204, the gyroscope 206, the communication module 208 and firmware 210. In the illustrated embodiment, the motion sensing device 104 connects wirelessly to the host device 110 and is powered by a battery.

Hand Controller Example

Figure 2C:
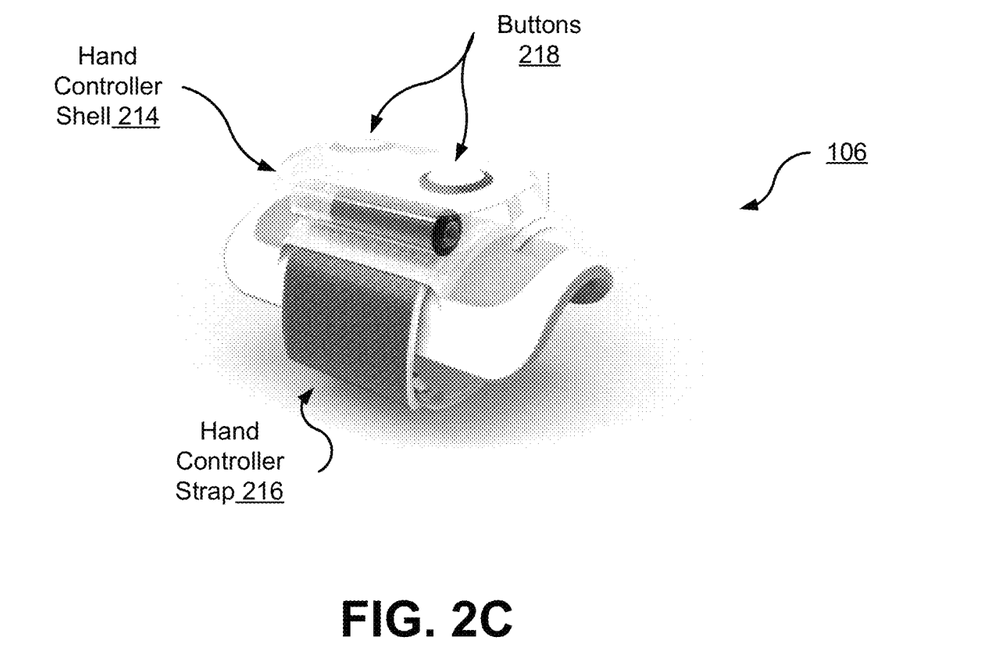
FIG. 2C illustrates a hand controller, according to one embodiment.

FIG. 2C illustrates a hand controller 106, according to one example embodiment. In this embodiment the hand controller 106 is comprised of an attaching mechanism 216, a hand controller shell 214 and buttons 218. Apart from buttons 218 the hand controller may also include a directional pad or joystick either in addition to or in place of the buttons 218. As described above with reference to FIG. 1, the hand controller 106 communicates with the host device 110. In the illustrated embodiment, the hand controller 106 communicates wirelessly and is battery powered.

In one embodiment, the attaching mechanism 216 is used to attach the hand controller to the fitness system or the user. For example, the attaching mechanism 216 is a strap used to strap the hand controller 106 onto the handle bar of an elliptical machine. In other embodiments, the attaching mechanism is not limited to a strap. In one embodiment, the hand controller shell 214 houses the electronic components of the hand controller 106 and other relevant components such as a battery. The form factor of the hand controller shell 214 facilitates the attaching of the hand controller 106 to the user or the fitness system. In one embodiment, the buttons 218 on the hand controller 106 receive user input.

Internally, the hand controller 106 includes a radio and a microcontroller. In one embodiment, the radio is an RF radio that connects to the motion sensing device 104 and sends an input signal to the motion sensing device 104 to be relayed to the host device 110. In an alternative embodiment, the hand controller includes a Bluetooth Low Energy (BLE) radio and a system on a chip (SoC). In some embodiments, the radio, microcontroller, and any other electronic components of the hand controller 106 may be placed on a single printed circuit board.

Figure 2D:
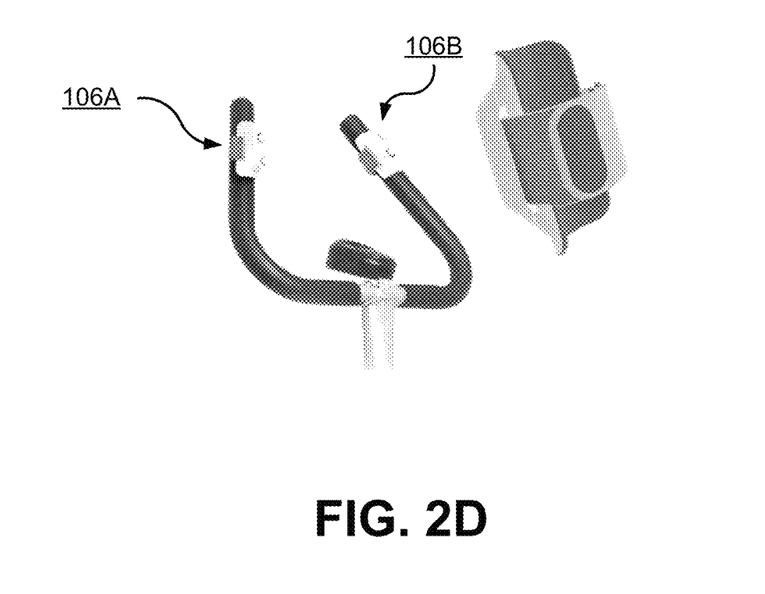
FIG. 2D illustrates an example of hand controllers mounted to handlebars of a fitness device, according to one embodiment.

FIG. 2D illustrates an example of hand controllers 106A, 106B mounted to handlebars of a fitness device, according to one embodiment. The straps 216 of the hand controllers 106A, 106B are wrapped around the handlebars. In one embodiment, the bottom side of the hand controller shell 214 may include an adhesive substance to increase the friction between the hand controllers 106A, 106B and the handlebars.

To reduce manufacturing costs, some or all of the components of the two hand controllers 106A, 106B may be identical. In one embodiment, the two hand controllers 106A, 106B are completely identical (e.g., same mechanical enclosure, internal electronics, and firmware). In this embodiment, it may be difficult for the firmware 210 or the host device API 112 to distinguish between the two hand controllers, and the interface software 111 may prompt the user to identify each hand controller as described above with reference to FIG. 1. In another embodiment, the two hand controllers have the same internal electronics (e.g., the same microcontroller, radio, etc), but may be placed in different enclosures to identify one controller as the left hand controller 106A and the other as the right hand controller 106B. For example, the buttons 218 on the two hand controllers may have a different layout or different colors, or the housings may have symmetric ergonomic features so that they are better suited for a user's hands. The two hand controllers 106 may also be flashed with different firmware so that the motion sensing device 104 or host device API 112 can distinguish between the input data from the two controllers 106. For example, the firmware on the left hand controller 106A may be configured to send an identifier (e.g., a binary 0) in a header of its input stream, while the firmware on the second hand controller 106B may be configured to send a different identifier (e.g., a binary 1) in a header of its input stream.

Figure 3:
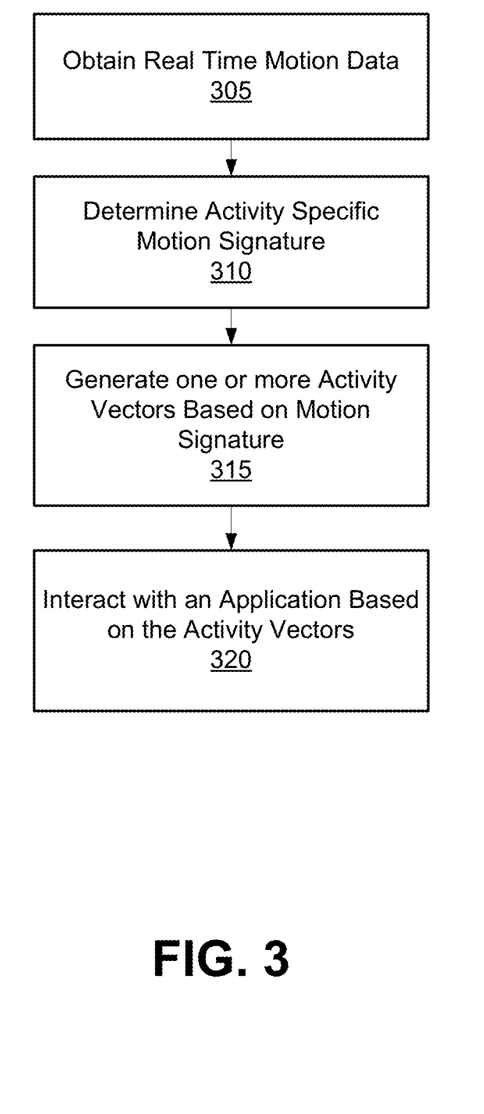
FIG. 3 is a flowchart illustrating an example process for interacting with a fitness application based on the user's interaction with the fitness system, according to one embodiment.

FIG. 3 is a flowchart illustrating an example process for interacting with a fitness application 114 based on the user's interaction with the fitness system, according to one embodiment. The user begins by attaching the hardware devices 102 to a fitness device or to the user's body; the hand controllers 106A, 106B can either be held in the user's hands or attached to the fitness device, and the motion sensing device 104 may be attached to the user's body or to the fitness device, depending on which fitness application 114 the user selects. One of the fitness applications 114 may be an instruction application that displays instructions for mounting the hardware devices 102 on a selected fitness device.

In one embodiment, the motion sensing device 104 obtains 305 real time motion data comprised of acceleration data from the accelerometer 204 and rotation data from the gyroscope 206, as the user interacts with the fitness system. The fitness system is not limited to a stationary exercise machine such as a treadmill, but may also include dynamic means of exercise, such as running on the road. The data obtained by the motion sensing device is 104 is transmitted to the host device 110 over established communication links 108.

Based on the data obtained 305, the interface software 111 on the host device determine 310 an activity specific motion signature. The activity specific motion signature identifies the current activity performed by the user. In one embodiment, the motion signature acts as a basis against which future movements performed by the user are compared against by the fitness applications 114.

In one embodiment, the interface software 111 generates one or more activity vectors 315 based on the motion signature. The activity vectors represent metrics associated with the activity level of the user. For example, the activity vectors may represent the number of calories burned by a user, the distance covered over a specific time interval or the intensity level of the user. The activity vectors are a standard unit of measurement across different types of fitness devices.

In one embodiment, the user interacts 320 with the fitness application 114 based on the activity vector generated 315 by the interface software 111. By altering the intensity with which a user performs a fitness activity, the user changes the activity vector over a period of time. The change in the activity vector alters the state of an object in the fitness application 114, or the behavior of the object in the fitness application 114 thereby allowing the user to interact with the fitness application 114 on the host device 110. For example, if the user is playing a running video game, where the user's character is running on the screen through an obstacle course, the intensity at which the user runs on the treadmill or cycles on a bicycle influences the speed at which the user's character (the object in an application 114) runs across the screen (behavior exhibited by the object) in the video game. Thus by running faster, the user changes the activity vector in real time, corresponding to an increase in speed of the user's character. The user may also interact with the application based on input from the hand controllers 106. For example, the user could press a button on the hand controller 106 as the user's character approaches an obstacle in the video game, causing the user's character to jump over or avoid the obstacle.

Figure 4:
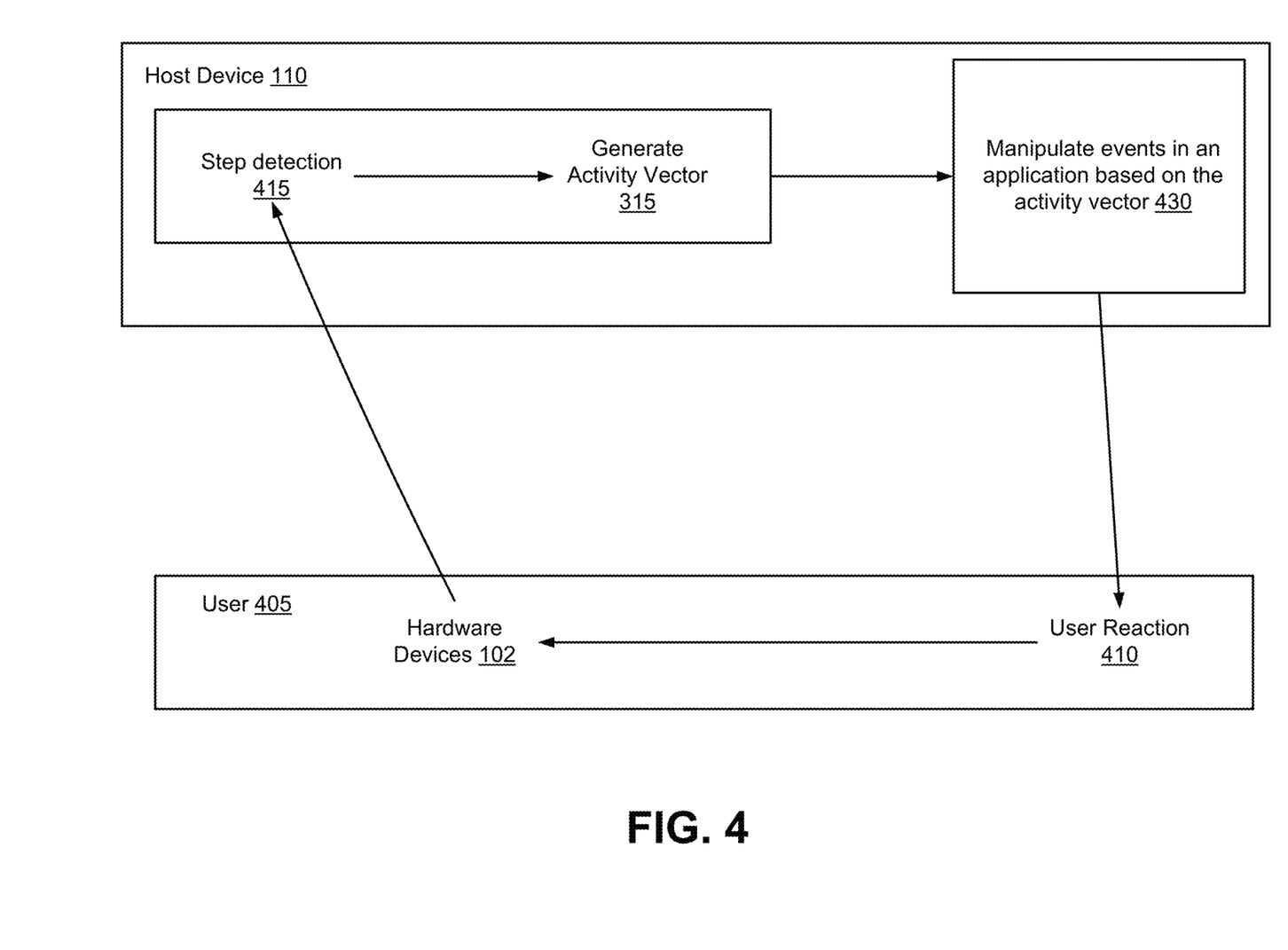
FIG. 4 illustrates an example process of a user manipulating events in a fitness application based on the user's interaction with the fitness system in real time, according to one embodiment.

FIG. 4 illustrates an example process of a user 405 manipulating events in a fitness application 114 based on the user's 405 interaction with the fitness system in real time, according to one embodiment. In this embodiment, the events in a fitness application 114 may influence a user reaction 410. The user reaction 410 is any change in user activity or intensity of the fitness activity performed by the user 405. For example, the user 405 may notice that the user's character in a video game is not running fast enough to avoid a disaster. This may generate the user reaction 410, where the user 405 begins to run faster while running on a treadmill. In other, embodiments the user 405 may make no change to the intensity at which the user 405 performs a fitness activity.

The hardware devices 102 capture motion data and input data to the hand controllers as the user 405 performs the fitness activity. In one embodiment, the user reaction 410 generates an increase in the magnitude of the motion data captured by the hardware devices 102, as compared to previous motion data captured by the hardware devices 102. The hardware devices 102 transmit the captured data to the host device 110 over communication links 108.

The interface software 111 on the host device 110 processes the motion data captured by the hardware devices 102. In one embodiment, the interface software 111, executes a step detection 415 function, to determine the steps taken by a user 405 over a time period. The step detection is performed using the activity specific motion signature 310 determined by the interface software 111, as a basis. In one embodiment, a step represents a unit of movement of the fitness activity performed by the user 405. For example, a single step while walking and running, or a single rotation of a bicycle pedal while cycling would be detected 415 as a single step by the interface software 111.

In one embodiment, the interface software 111 generates an activity vector 345 based on the number of steps over a time window, or a time span over which a single step takes place. The motion signature of the activity performed by the user 405, determines how the number of steps over a specific time window, or the time between two steps influences the value of the activity vector. For example, one revolution on a bicycle may be considered as 2 steps while running. Thus, the interface software 111, identifies what activity a step is related to based on the motion signature determined by the interface software 111. Then the interface software 111 modifies or generates the activity vector based on the number of steps in a given time window, or the time between steps and the motion signature associated with the step. This allows the user 405 to switch between fitness machines, such as move from running on a treadmill to cycling on a fitness bicycle, but still generate consistent activity vectors representing the intensity at which the user 405 performs different fitness activities across different fitness machines.

In one embodiment, the number of steps within a given time window represents the motion signature associated with a fitness activity. For example, running may correspond to fewer steps being detected in the given time window as compared to bicycling. In another embodiment, the activity vector is an intensity level that is scaled inversely to the time between steps for a specific motion signature. For example, if the time between steps is 0.5 seconds the intensity level is given a value of 5 (on a scale of 0 to 10). However, when the time between steps reduces to 0.4, the intensity level is given a value of 7 (on a scale of 0 to 10). In a different embodiment, the activity vector is an intensity level inversely to the number of steps in a given time window.

Based on the activity vector the user 405 manipulates events in the fitness application 114 in real time. In one embodiment, elements or objects in the fitness application 114 are given attributes based on the activity vector generated 315 by the interface software 111. For example, the fitness application 114 may be a game, where the rate at which points are earned by the user 405 increases as the magnitude of the activity vector increases. Hence, the user 405 may run faster on a treadmill to increase the number of steps per given time window, thereby increasing the magnitude of the generated activity vector, manipulating 430 the rate at which points are increased in the game.

Figure 5:
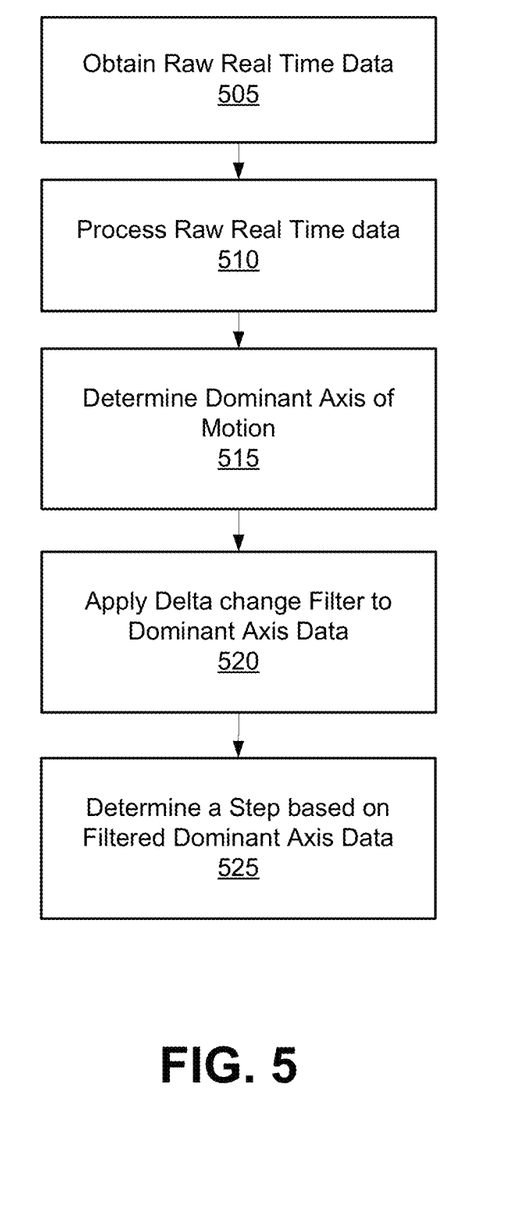
FIG. 5 is a flow chart illustrating an example process for determining a step taken by the user, based on motion data, according to one embodiment

FIG. 5 is a flow chart illustrating an example process for determining a step taken by the user, based on motion data, according to one embodiment. The hardware devices 102 obtain 505 raw real time motion data as the user performs the fitness activity. The hardware devices 102 transmit the raw motion data to the host device 110 and interface software 111 over communication links 108.

In one embodiment, the interface software 111 processes 510 the raw motion data. There are a number of techniques that may be applied to process 510 the raw motion data. For example, the interface software may use a high pass filter 510 to process the raw motion data on each axis of motion or rotation. The high pass filter attenuates or reduces the magnitude of data with frequencies below a cutoff frequency.

In one embodiment, the interface software 111 determines 515 a dominant axis of the processed motion data. The dominant axis represents the axis along which there is most motion captured by the hardware devices 102, as the user performs the fitness activity. Determining 515 the dominant axis of motion, helps the interface software 111 identify the primary direction or axis of motion of the user as the user performs a fitness activity. In one embodiment, the primary direction of motion of the user influences at least in part the motion signature generated by the interface software 111.

In one embodiment, the dominant axis is determined 515 by summing the absolute value of each axis of processed motion data over a rolling time window. In one embodiment, the axis with the largest absolute value over the rolling time window is picked as the dominant axis of motion. If a good set of data is not obtained for the current dominant axis, the dominant axis is changed to the axis with the next largest absolute value. In one embodiment, a good set of data is determined by comparing the ratio of the absolute value of the current dominant axis to the sum of the absolute values of the other axes, and a threshold value.

In one embodiment, a delta change filter is applied 520 to the dominant axis of the processed 510 motion data. The delta change filter increases or decreases the difference between a current value and in a time series of motion data and a previous value in the time series. For example, if the current value of the processed motion data is similar to the previous value in the time series, the delta change filter changes the current value in the time series to equal that of the previous value. If the current value is significantly different from the previous value the delta change filter changes the current value by an interpolated amount so that the difference between the current value and the previous value increases (i.e., the absolute difference).

In one embodiment, the interface software 111 determines 525 the step taken by the user based on the time series of the processed data along the dominant axis of motion. For example, a step is detected 525 when there is a sign change in the acceleration data of the determined 520 dominant axis. In another embodiment, an acceleration threshold must be crossed just before the sign change in the acceleration data, for the step to be considered a potential step. For example, the time series acceleration value must be greater than 0.5 G, before a sign change is identified in a time window containing 20 accelerometer samples collected over 333 milliseconds (ms).

Figure 6:
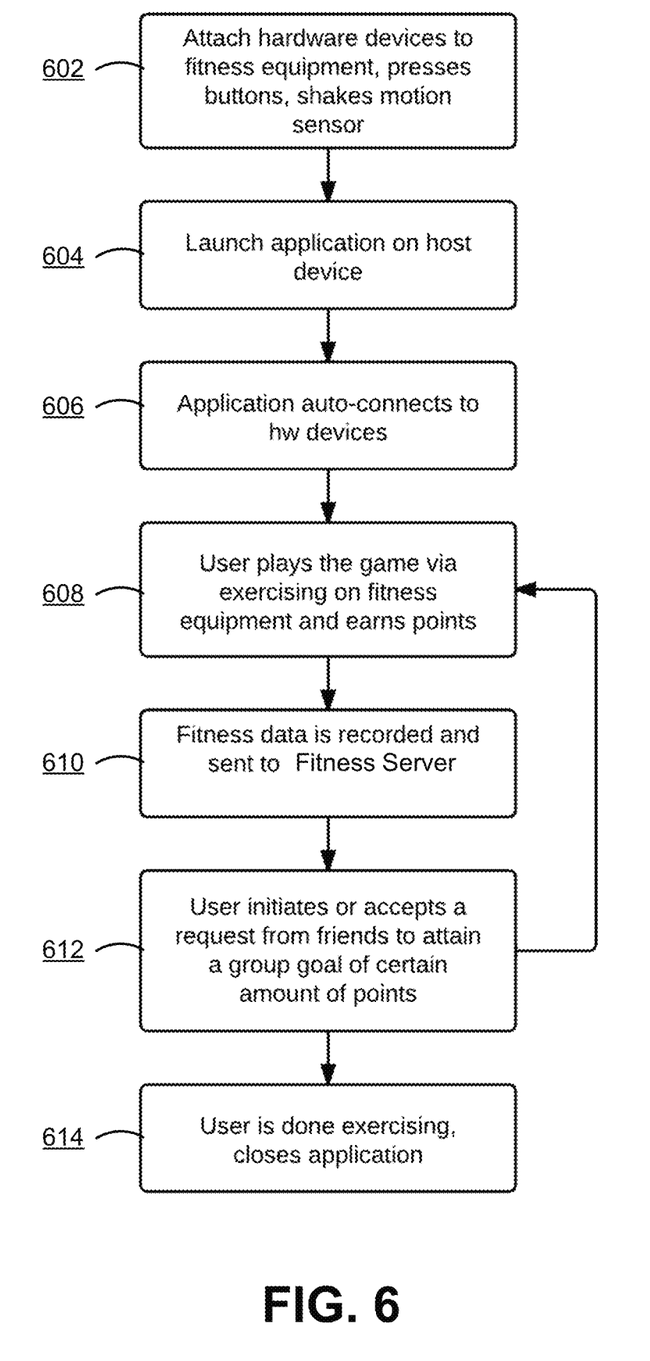
FIG. 6 is a flow chart illustrating an example process for interacting with the adaptable fitness system, according to one embodiment.

FIG. 6 is a flow chart illustrating an example process for interacting with the adaptable fitness system, according to one embodiment.

The user begins by attaching 602 the hardware devices 102 to a fitness device or to the user's body; the hand controllers 106A, 106B can either be held in the user's hands or attached to the fitness device, and the motion sensing device 104 may be attached to the user's body or to the fitness device, depending on which fitness application 114 the user selects. One of the fitness applications 114 may be an instruction application that displays instructions for mounting the hardware devices 102 on a selected fitness device.

Next, the user selects and launches 604 a fitness application 114, and the host device API 112 initiates a search to auto-connect 606 with the hardware devices 102, which runs in the background. The application 114 provides a user interface indicator showing the state in which the hardware devices 102 are connecting.

The user then begins to interact 608 with the application 114. As the user works out, the motion sensing device 104 sends input data to the application 114 tracking player movement. The hand controllers 106A, 106B send input data to the application tracking player game inputs. The application 114 shows the user game cues and feedback. The operating system of the host device 110 runs the application.

The host device 110 records 610 fitness data for the user to review. The fitness data is reflected in quantifiers such as steps taken and calories burned. The user is encouraged to exercise by seeing his game progression and fitness data.

The application 114 may optionally use the host device API 112 to send the fitness data to the fitness server 118 to be saved. If the host device 110 does not have network connectivity at the time the fitness data is recorded 610, then the data may be automatically sent when network connectivity becomes available. If the user chooses to use the fitness application 114 anonymously (i.e., without logging in to a user account), then the user's session is tracked anonymously.

The user is also able to share his game progression and fitness data online with friends on social networking systems, which provides further encouragement. In addition, the user may use social features of the fitness server 118, such as initiating/accepting requests 612 to attain a group goal (e.g., a specified number of movement units) or initiating/accepting challenges to attain an individual goal. If a request or challenge is activated, then the user begins interacting 508 with the application 114 again.

When the user is done, the user ends the session by closing 614 the application 114.

In one embodiment, the user can create a personal goal to achieve an activity vector value in a given time period. For example, a goal can be to run 50 miles in one week, while maintaining an intensity level of 7 (based on an intensity level scale ranging from 0 to 10). These personal goals can then be shared with friends within a social network.

Users can create also cooperative goals for a group in a social network to achieve an activity vector value. For example, a group of five people may set a goal to achieve 250 miles for the week, while all maintaining the intensity level of 7.

Activity vectors can also be used as a basis for activities that benefit from normalization of data for comparison purposes. For example, activity vectors can be used in competitions between groups or friends in a network. Challenges can be issued and broadcast to a user's friends on social network.

Computing Machine Architecture

Figure 7:
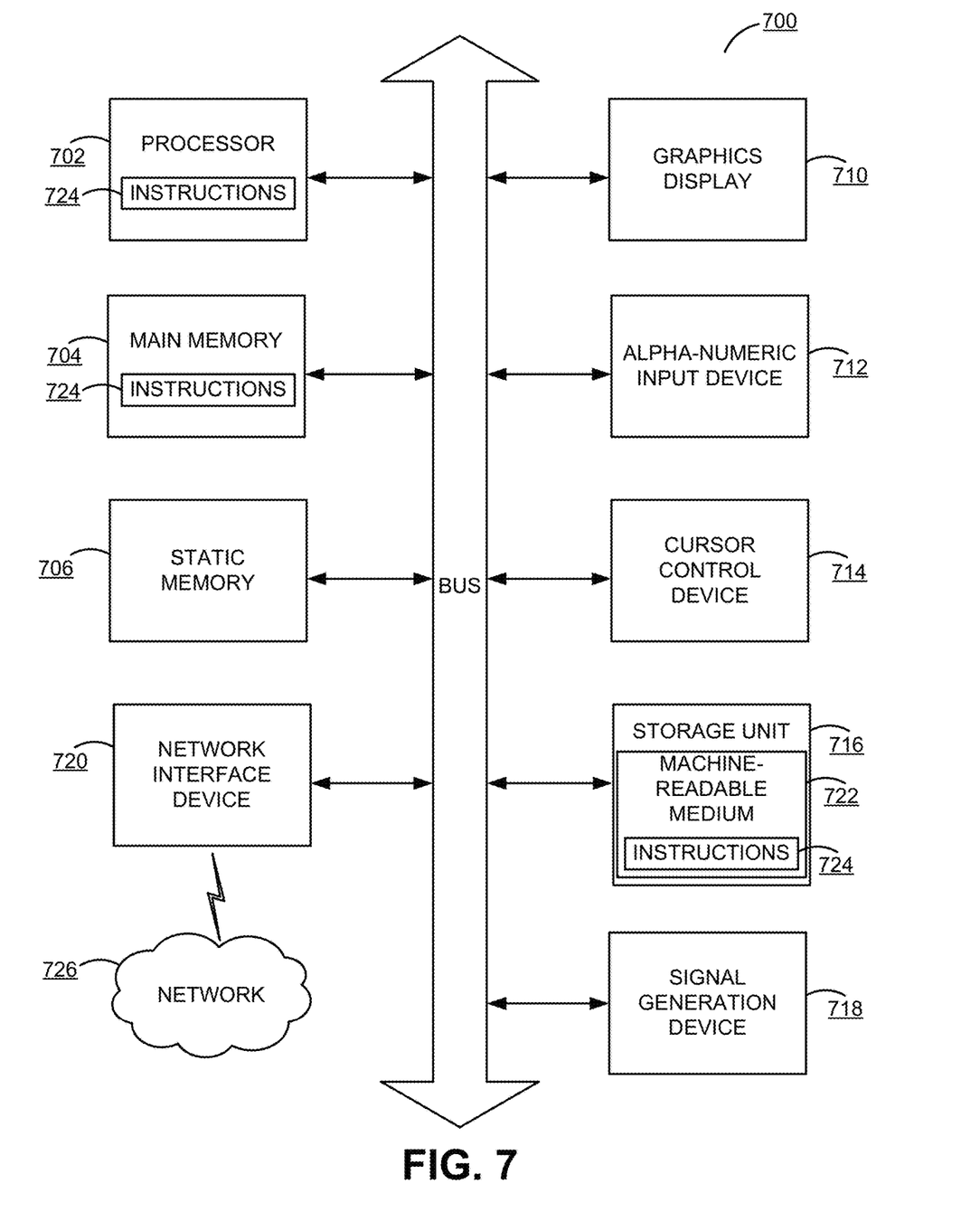
FIG. 7 illustrates one embodiment of components of an example machine able to read instructions from a machine-readable medium and execute them in a processor (or controller).

FIG. 7 is a block diagram illustrating components of an example machine able to read instructions from a machine-readable medium and execute them in a processor (or controller). The example machine illustrated in FIG. 7 may be used, for example, as the host device 110 or the fitness server 118 shown in FIG. 1. Specifically, FIG. 7 shows a diagrammatic representation of a machine in the example form of a computer system 700 within which instructions 724 (e.g., software) for causing the machine to perform any one or more of the methodologies discussed herein may be executed. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 724 (sequential or otherwise) that specify actions to be taken by that machine. Further, while only a single machine is illustrated, the term "machine" shall also be taken to include any collection of machines that individually or jointly execute instructions 724 to perform any one or more of the methodologies discussed herein.

The example computer system 700 includes a processor 702 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 704, and a static memory 706, which are configured to communicate with each other via a bus 708. The computer system 700 may further include graphics display unit 710 (e.g., a plasma display panel (PDP), a liquid crystal display (LCD), a projector, or a cathode ray tube (CRT)). The computer system 700 may also include alphanumeric input device 712 (e.g., a keyboard), a cursor control device 714 (e.g., a mouse, a trackball, a joystick, a motion sensor, or other pointing instrument), a storage unit 716, a signal generation device 718 (e.g., a speaker), and a network interface device 720, which also are configured to communicate via the bus 708.

The storage unit 716 includes a machine-readable medium 722 on which is stored instructions 724 (e.g., software) embodying any one or more of the methodologies or functions described herein. The instructions 724 (e.g., software) may also reside, completely or at least partially, within the main memory 704 or within the processor 702 (e.g., within a processor's cache memory) during execution thereof by the computer system 700, the main memory 704 and the processor 702 also constituting machine-readable media. The instructions 724 (e.g., software) may be transmitted or received over a network 726 via the network interface device 720.

While machine-readable medium 722 is shown in an example embodiment to be a single medium, the term "machine-readable medium" should be taken to include a single medium or multiple media (e.g., a centralized or distributed database, or associated caches and servers) able to store instructions (e.g., instructions 724). The term "machine-readable medium" shall also be taken to include any medium that is capable of storing instructions (e.g., instructions 724) for execution by the machine and that cause the machine to perform any one or more of the methodologies disclosed herein. The term "machine-readable medium" includes, but not be limited to, data repositories in the form of solid-state memories, optical media, and magnetic media.

Additional Configuration Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for controlling an application with a fitness device through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A system for adapting a fitness device into a game controller, comprising:
a motion sensor configured to:
sense motion of the fitness device user;
and transmit a first dataset comprising real-time motion data information to a host device; and
one or more controllers configured to receive manual game control input from a user and transmit a second dataset comprising game control input to a host device;
a fitness server comprising a cloud services module, a fitness database, and an application database, wherein the fitness server is configured to:
store historical fitness data from a user in the fitness database, the historical fitness data comprising physical activity and game performance data;
receive connections from a host device;
allow the host device to download game applications;
receive intensity of effort data for the user from the host device; and
update the user's historical data in the fitness database with the intensity of effort data; and
a host device comprising a memory, a processor, and a plurality of programming instructions stored in the memory which, when operating on the processor, cause the host device to:
connect with the fitness server;
download and operate a game application from the application database on the fitness server, the game application configured to receive inputs, change its operation in response to the inputs, and display a visual output corresponding to the changed operation;
retrieve the historical data for the user from the fitness database on the fitness server;
receive the first dataset comprising real-time motion data information from the motion sensor;
receive the second dataset comprising game control input from the one or more controllers;
determine, based on the first dataset and the historical data, a motion signature representing a recurring movement related to a fitness activity;
create an activity vector representing the motion signature;
calculate intensity of effort data from the activity vector;
send the intensity of effort data to the fitness server;
send the activity vector to the game application as movement input;
send the second dataset to the game application as action input;
display the visual output from the game application to the fitness device user.

2. The system of claim 1, wherein the cloud services module of the fitness server is configured to:
receive connections from a plurality of host devices; and
coordinate the game application states on a plurality of host devices.

* * * * *